United States Patent [19]

Lande

[11] 4,177,523
[45] Dec. 11, 1979

[54] ARTIFICIAL HEART

[76] Inventor: Arnold J. Landé, 2145 Stanmore Dr., Houston, Tex. 77019

[21] Appl. No.: 886,824

[22] Filed: Mar. 15, 1978

[51] Int. Cl.² .......................... A61F 1/24; A61M 1/03
[52] U.S. Cl. ........................................ 3/1.7; 128/1 D
[58] Field of Search .......... 3/1.7, 1; 128/1 D, DIG. 3

[56] References Cited

U.S. PATENT DOCUMENTS

| 3,641,591 | 2/1972 | Kolff | 3/1.7 |
|---|---|---|---|
| 3,831,203 | 8/1974 | Ridgway | 3/1.7 |
| 4,015,590 | 4/1977 | Normann | 128/1 D |
| 4,058,857 | 11/1977 | Runge et al. | 3/1.7 |

FOREIGN PATENT DOCUMENTS 1538644  7/1968  France ........................................ 3/1.7

*Primary Examiner*—Ronald L. Frinks
*Attorney, Agent, or Firm*—Michael L. Parks

[57] ABSTRACT

This invention relates to a fluid driven blood pumping apparatus for use as an artificial heart. This apparatus may be used as a temporary mechanical replacement or a permanent mechanical replacement for a malfunctioning heart. The apparatus of this invention comprises a 1st pumping chamber having expandable walls which has an inlet for receiving blood and an outlet for discharging blood, a 2nd pumping chamber positioned within the 1st pumping chamber having expandable walls and having an inlet for receiving blood and an outlet for discharging blood, an inflatable blood displacement member having expandable walls positioned within the 2nd pumping chamber for periodic inflation and deflation to discharge and receive blood in the 2nd pumping chamber for periodic expansion and contraction of the 2nd pumping chamber walls for discharging and receiving blood in the 1st pumping chamber and an expandable and contractable core member positioned within the inflatable blood displacement member for providing volume adjustments of the inflatable blood displacement member.

6 Claims, 6 Drawing Figures

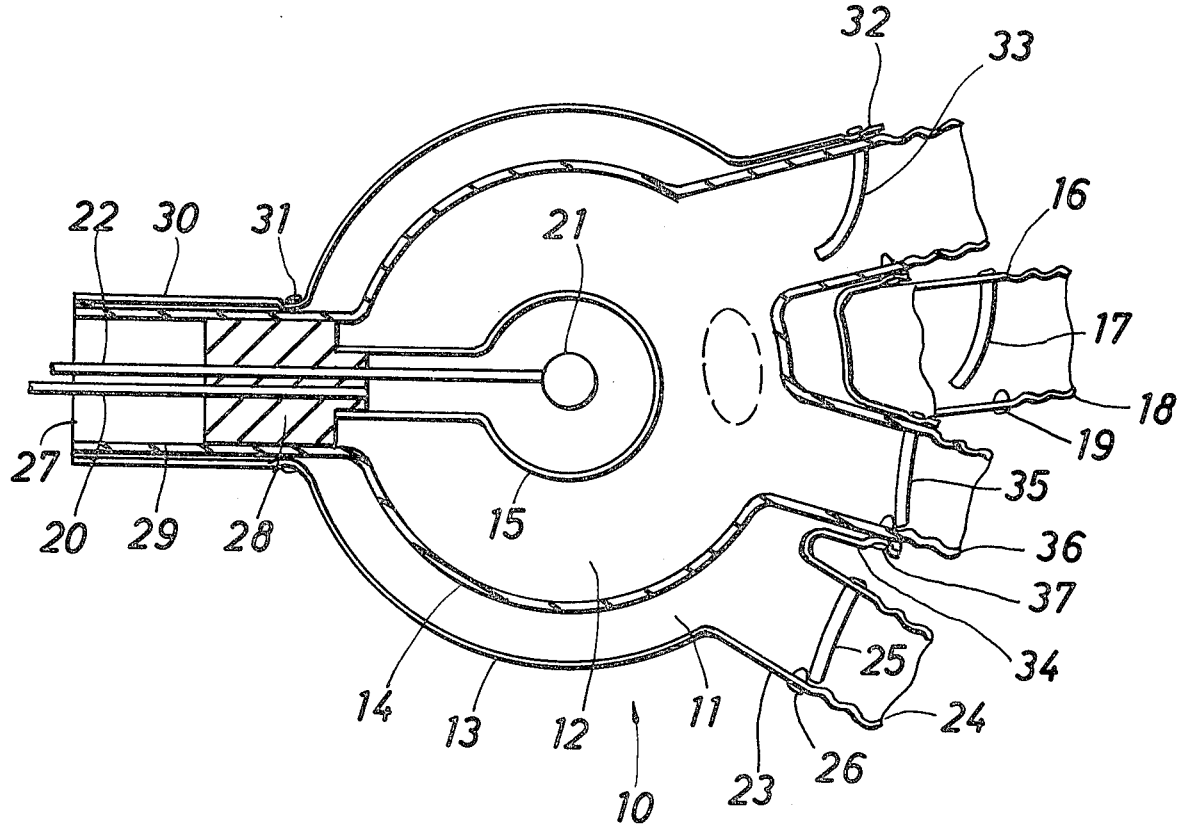

ARTIFICIAL HEART

BACKGROUND OF THE INVENTION

This invention relates to a fluid driven blood pumping apparatus for use as an artificial heart. The apparatus of this invention is substantially flexible and fits well into the chest cavity of a patient for either temporary or permanent implantation.

Devices, such as U.S. Pat. Nos. 3,641,591 and 4,015,590, are known which use pneumatic or hydraulic pressures as a motive force to activate artificial hearts, or heart-assist devices for pumping blood.

The prior art devices, however, have been complex usually requiring two separate pressure sources, one for the artificial right ventricle and one for the artificial left ventricle with the corresponding duplication of the controls to provide the correct discharge pressures for each chamber and the coordination problems associated with working two separate pressure sources at different pressures.

Many of the artificial hearts which use atomic power or other elevated temperature power sources to drive them have a problem with dissipating the heat generated so that surrounding tissues may be heated which is not totally desirable.

Also, many of the prior art apparatus have had stress points within the internal working parts of the heart pump which caused stress failures in the parts and thus inhibited their use for fear of their failure.

As clotting of the blood in many of the artificial hearts has been a real danger and problem, the prior art has attempted many ways to prevent clotting. As stagnation in any part of the artificial heart can lead to potential clotting, the prior art has tried numerous ways to prevent stagnation of the blood, but these have been only partially successful.

Further, many of the prior art devices have fixed rigid walls which cause problems during the surgical procedure required to implant the device and thus required a greater trauma to the patient during surgical implantation. Also many of the fixed wall heart pumps have a fixed capacity volume which cannot be varied to allow for increased blood flow rates or decreased flow rates without necessarily increasing or decreasing the rate of the pumping or volume of the driving fluid used.

Many of the prior art devices have been very expensive and extremely complex.

Also in the fixed wall artificial heart no cardiac massage could be performed should a failure of the artificial heart occur.

OBJECTS OF THE INVENTION

It is the object of this invention to provide an artificial heart pump using only a single pressure driving system to drive both the artificial right and left ventricle.

It is a further object of this invention to provide an artificial heart which provides for increased capacity and decreased capacity of the pumping chambers without necessarily adjusting the rate of pumping or volume of driving fluid without affecting the efficiency of operation of the artificial heart.

Also it is an object of this invention to provide an artificial heart which is very flexible for easy surgical implantation with minimal trauma to the patient.

Yet another object of this invention is to provide an artificial heart which has few stress points for longer wear and little or no stagnation of the blood flow to prevent clotting.

Still a further object of this invention is to provide an artificial heart which is relatively simple and inexpensive.

It is also an object to provide pressures which are safe for the patients pulmonary and systemic circulatory system and are not subject to being over-pressured.

It is also to provide an artificial heart which if implanted and failure occurred external heart massage could be performed.

It is a further object to provide an artificial heart which obeys Starling's Law that the heart pumps harder when more blood comes to it.

It is an object of this invention to provide an artificial heart which can dissipate the heat which may be generated by the power source through the circulation system of the body.

Figure 1:
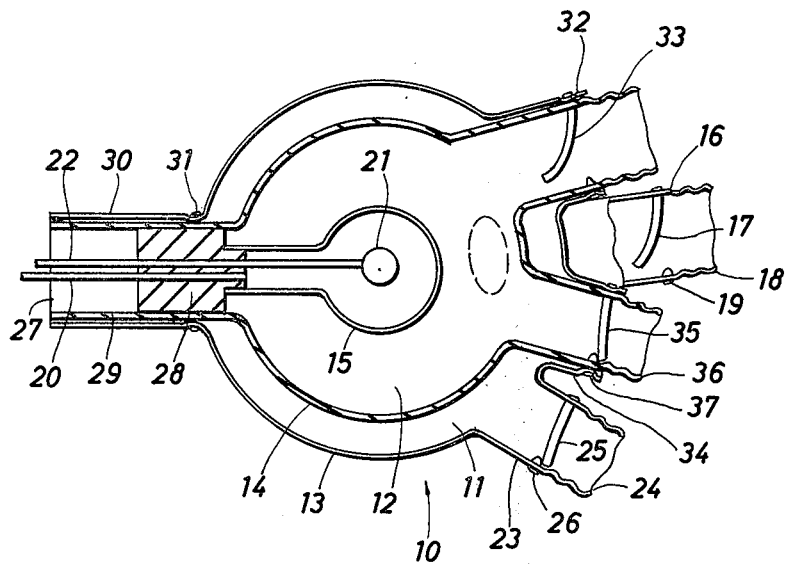
FIG. 1 is a cross sectional view of the artificial heart of this invention with the inflatable blood displacement member in a relatively deflated position.

Referring now to the drawings and particularly to FIG. 1, the apparatus of this invention is generally referred to at reference numeral 10. This invention 10 has a 1st pumping chamber 11 which is formed between expandable walls 13 and 14. Further, this invention 10 has a 2nd pumping chamber 12 which is formed between expandable wall 14 and an inflatable blood displacement member 15. These 1st and 2nd pumping chambers 11 and 12 are for receiving blood and pumping the blood out of these chambers. The blood is pumped out of 2nd pumping chamber 12 by the expansion of inflatable blood displacement member 15 being filled with a fluid, such as a gas or liquid, by way of a tube 20 which is connected to any source of a fluid oscillator (not shown) for 1st injecting and then flowing the fluid out. Also mounted within the inflatable blood displacement member 15 is an expandable and contractable core member 21 which can be expanded or contracted as desired by the introduction or withdrawal of fluid to make volume adjustments in the expandable and contractable core member 21 for corresponding volume adjustments in the volume of the inflatable blood displacement member 15. The fluid introduced to the expandable and contractable core member 21 is introduced by way of tube 22 which is connected to any standard source of fluid feed control (not shown) for injecting fluid or removal of fluid.

The tubes 20 and 22 are passed through a channel 27 and stopper seal 28. The channel 27 is formed by channels 29 and 30 which are formed from extended portions of the expandable walls 13 and 14 of the 1st and 2nd pumping chambers 11 and 12. The stopper seal 28 is fixed in place in the channel 27 flush with the expandable walls 14 so that no place for stagnation of the blood can occur in the 2nd pumping chamber. A suture 31 is placed about the expandable walls 13 and 14 forming the channels 29 and 30 to seal the expandable walls 13 and 14 and fix the stopper seal 28 in place.

The blood is received into the 1st pumping chamber 11 through the right atrium of the heart (not shown) by flowing through inlet 16 and a 1st single directional flow valve 17. The inlet 16 is lined with attaching fiber 18 for attachment to the patients right atrium. The 1st single directional flow valve 17 is mounted in the inlet 16 against the attaching fiber 18 by an encircling suture 19. In FIG. 1 the single directional flow valve 17 would be in an open position for filling the 1st pumping chamber 11, as the inflatable blood displacement member 15 and expandable walls 13 and 14 are in non-expanded positions.

Figure 2:
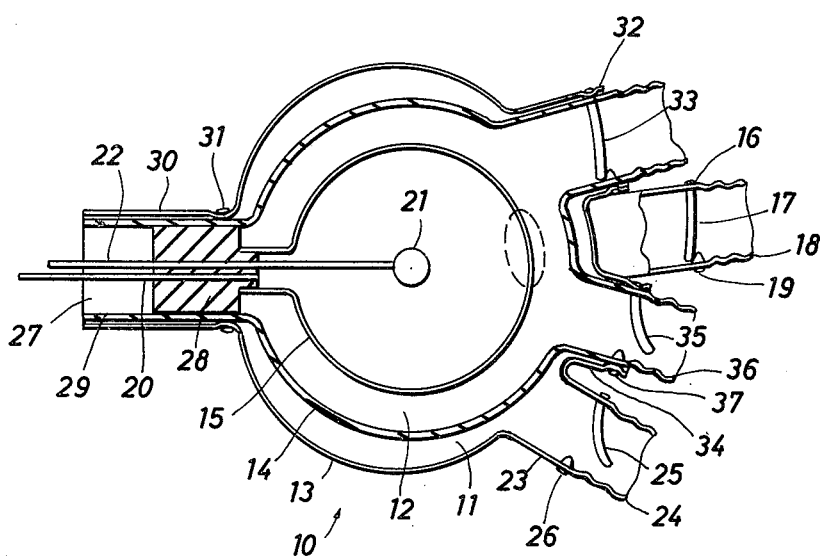
FIG. 2 is a cross sectional view of the artificial heart of this invention with the inflatable blood displacement member in the later stages of being inflated, and having further caused the expansion of 1st pumping chamber and 2nd pumping chamber.

In FIG. 2 the inflatable blood displacement member 15 is expanded by flowing fluid through the tube 20 to expand the inflatable blood displacement member 15 and drive the blood in the 2nd pumping chamber 12 toward the expandable wall 13 which thus drives the blood in the 1st pumping chamber out of an outlet 23 and a 2nd single directional flow valve 25. The outlet 23 is lined with attaching fiber 24 for attachment to the patients pulmonary artery (not shown). The 2nd single directional flow valve 25 is mounted in the outlet 23 against the attaching fiber 24 by encircling suture 26. The blood discharged to the pulmonary arteries is circulated through the pulmonary system and returned by way of the pulmonary veins and left atrium for inflow into inlet 32 and through the 3rd single directional flow valve 33. In FIG. 1, 3rd single directional flow valve 33 would be open while in FIG. 2 the 3rd single directional flow valve 33 would be closed by the pressure of the blood generated in the 2nd pumping chamber 12 which would be driving blood out outlet 34 and through the 4th single directional flow valve 35. The outlet 34 is lined with attaching fiber 36 for attachment to the patient aorta (not shown). The 4th single directional flow valve 35 is mounted in the outlet 34 against the attaching fiber 36 by encircling suture 37.

Figure 3:
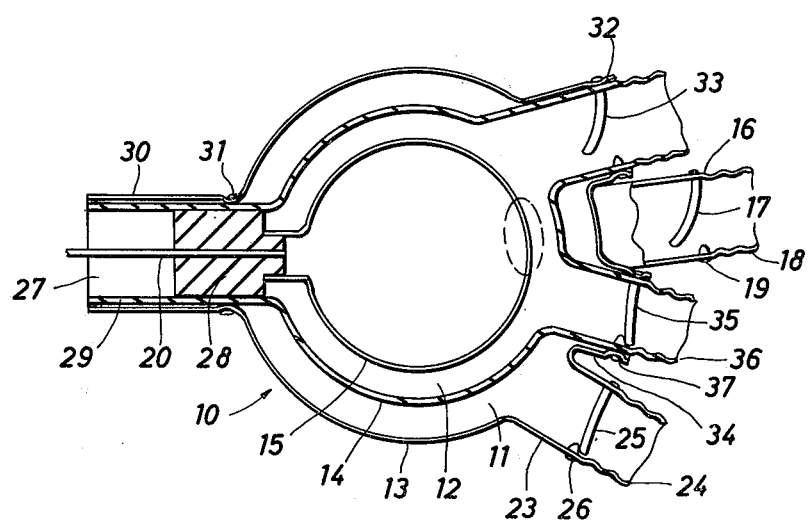
FIG. 3 is a cross sectional view of the artificial heart of this invention with the inflatable blood displacement member in the later stages of being deflated and the 1st and 2nd pumping chambers expandable walls contracting.
Figure 4:
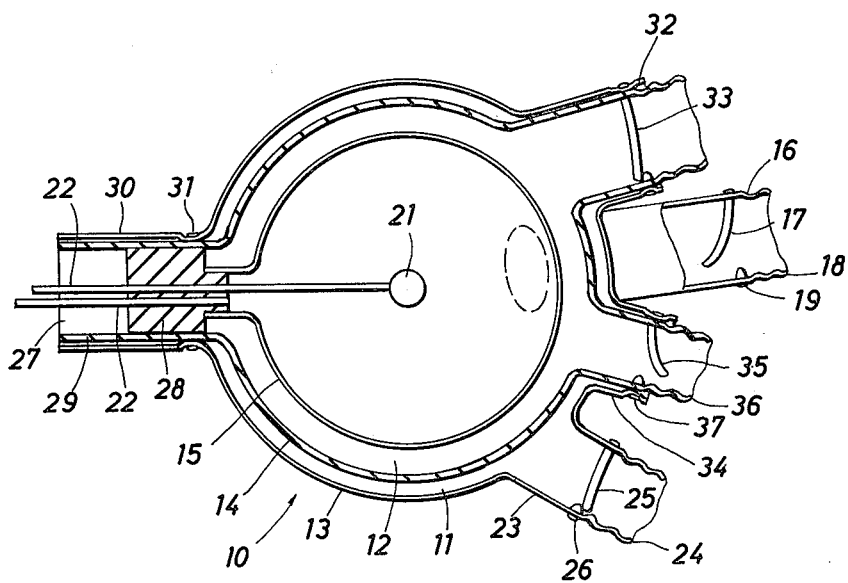
FIG. 4 is a cross sectional view of the artificial heart of this invention with the inflatable blood displacement member in an expanded position and having further caused the expansion of 1st pumping chamber and 2nd pumping chamber; and the expandable and contractable core member is in a contracted position to change the volume of the inflatable blood displacement member.

In at least one embodiment as shown in FIG. 3 the expandable and contractable core member 21 may be deleted if there is no desire to provide volume adjustments within the inflatable blood displacement member 15 by means of changing the volume of inflatable blood displacement member 15 by any other means than inflating or deflating the inflatable blood displacement member 15.

Figure 6:
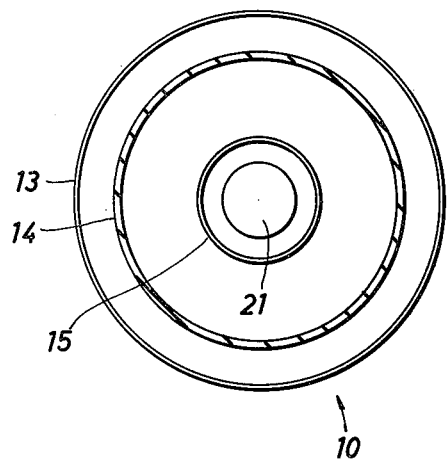
FIG. 6 is a cross sectional view of the artificial heart taken through Line 6—6.
Figure 5:
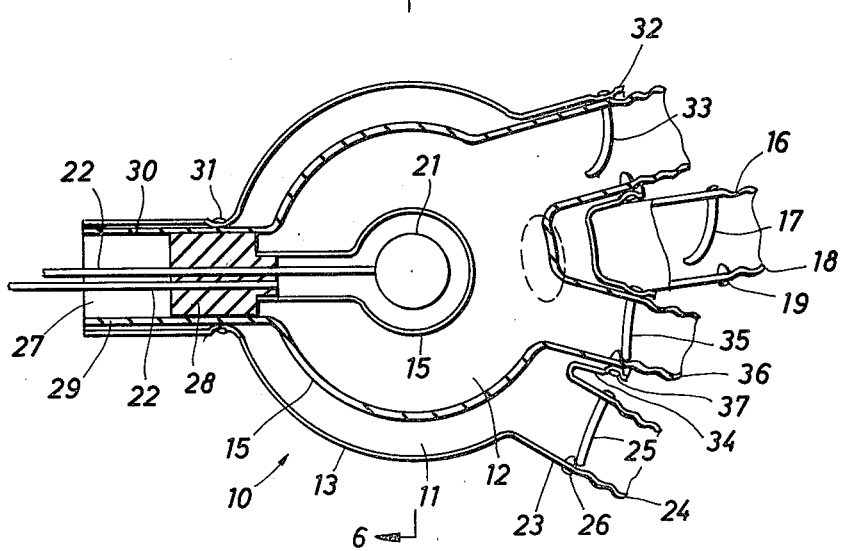
FIG. 5 is a cross sectional view of the artificial heart of this invention with the expandable and contractable core member partially expanded.

It should be understood from the foregoing that examples of the embodiments disclosed are substantially spherical in shape and are substantially elastic in character which thus provides an optimum of design with a minimum of fatigue for these relatively elastic materials such as Silastics, polyurethanes, rubber, etc. In these elastic materials above referred to by way of example of material for use in the 1st and 2nd pumping chambers, the materials used in the 1st pumping chamber must have sufficient resistance to expansion for producing pressures sufficient to drive blood through the pulmonary arteries when said 2nd pumping chamber is expanded. The material used in the 2nd pumping chamber must have sufficient resistance to expansion for producing pressures sufficient to drive blood through the aorta when said inflatable blood displacement means is expanded. Thus as these spheres, flexible walls 13 and 14, act each against the fluid contained therein, La Place's Law of $P=2T/R$ comes into play. La Place's Law states that the Pressure in a sphere relates to Tension which is dependent on composition and thickness of the material, and the Radius of the Sphere. Thus, the larger radius of 1st pumping chamber and in some embodiments the lower tension due either to thickness or composition of the material provides a 1st pumping chamber 11 which generates a lower pressure than the 2nd pumping chamber 12 which has a smaller radius. These lower pressures in 1st pumping chamber 11 and higher pressures in 2nd pumping chamber 12 being produced from a common driving pressure of the inflatable blood displacement member 15 follow La Place's law and give a dual pressure system from a common drive pressure. This concentric arrangement, as best shown in FIG. 6, of expandable and contractable core member 21 within inflatable blood displacement member 15 within expandable walls 14 within expandable walls 13, allows for the optimum operation of La Place's Law. Using La Place's Law, the 1st pumping chamber having expandable walls should produce pressures from $-10$ mm of mercury to 50 mm of mercury as combined with the expansion of said 2nd pumping chamber. While the 2nd pumping chamber having expandable walls should produce pressures from $-10$ mm of Mercury to 400 mm of Mercury in combination with the expansion of said inflatable blood displacement member. The inflatable blood displacement member should have expandable walls under a fluid pressure of from $-10$ mm of Mercury to 500 mm of Mercury. Further, this arrangement also makes possible the operation of Starling's Law, such that the heart pumps harder when more blood comes into it because in this configuration with expandable chambers, the artificial heart can take a greater volume of blood and still discharge that greater volume within the control limits.

Further, by changing the volume of the expandable and contractable core member 21 the effective volume of the inflatable blood displacement member 15 is changed which thereby adjusts the whole system.

Also this inflatable blood displacement member 15, when and if filled by a fluid which contained excessive heat, such as that generated by nuclear power sources, could be dissipated over the circulatory system.

The foregoing disclosure and description of the invention is illustrative and explanatory thereof, and various changes in the size, shape and materials as well as in the details of the illustrated construction may be made within the scope of the appended claims without departing from the spirit of the invention.

I claim:
1. A blood pumping apparatus for use as an artificial heart comprising;
   (a) a 1st pumping chamber having expandable walls and having an inlet for receiving blood and an outlet for discharging blood;
   (b) a 2nd pumping chamber positioned within said 1st pumping chamber having expandable walls and having an inlet for receiving blood and an outlet for discharging blood; and (c) an inflatable blood displacement means having expandable walls positioned within said 2nd pumping chamber for periodic inflation and deflation to discharge and receive blood in said 2nd pumping chamber and for periodic expansion and contraction of said 2nd pumping chamber walls for discharging and receiving blood in said 1st pumping chamber.

2. A blood pumping apparatus of claim 1 for use as an artificial heart further comprising an expandable and contractable core means positioned within said inflatable blood displacement means for providing volume adjustments in the capacity of said inflatable blood displacement means.

3. The blood pumping apparatus of claim 1, wherein
(a) said 1st pumping chamber having expandable walls has sufficient resistance to expansion for producing pressures sufficient to drive blood through the pulmonary arteries when said 2nd pumping chamber is expanded; and
(b) said 2nd pumping chamber having expandable walls has sufficient resistance to expansion for producing pressures sufficient to drive blood through the aorta when said inflatable blood displacement means is expanded.

4. The blood pumping apparatus of claim 3, further comprising:
(a) a flow means for flowing fluid into and from said inflatable blood displacement means through said 1st pumping chamber and said 2nd pumping chamber for inflation and deflation of said inflatable blood displacement means; and
(b) a means for flowing fluid into and from said expandable and contractable core means through said 1st pumping chambers; said 2nd pumping chamber; and said inflatable blood displacement means for providing volume adjustments in said expandable and contractable core means.

5. The blood pumping apparatus of claim 4, wherein:
(a) said 1st pumping chamber having expandable walls produces a pressure from −10 mm of Mercury to 50 mm of Mercury in combination with the expansion of said 2nd pumping chamber;
(b) said 2nd Pumping chamber having expandable walls produces a pressure from −10 mm of Mercury to 400 mm of Mercury in combination with the expansion of said inflatable blood displacement means; and
(c) said inflatable blood displacement means has expandable walls under a fluid pressure of from −10 mm of Mercury to 500 mm of Mercury.

6. The blood pumping apparatus of claim 5, further comprising:
(a) a 1st single directional flow valve connected to said inlet of said 1st pumping chamber for flowing blood into said 1st pumping chamber;
(b) a 2nd single directional flow valve connected to said outlet of said 1st pumping chamber for flowing blood out of said 1st pumping chamber;
(c) a 3rd single directional flow valve connected to said inlet of said 2nd pumping chamber for flowing blood into said 2nd pumping chamber; and
(d) a 4th single directional flow valve connected to said outlet of said 2nd pumping chamber for flowing blood out of said 2nd pumping chamber.

* * * * *